United States Patent
Chang et al.

(10) Patent No.: US 7,135,000 B2
(45) Date of Patent: Nov. 14, 2006

(54) HEART STATE MONITOR METHOD

(75) Inventors: Kuo-Yuan Chang, 1F, No. 11, Lane 139, Sec. 2, pei Hsin Rd., Hsin-Tien City, Taipei Hsien (TW); Kuo-Fu Chang, Chung Ho (TW); Chi Fang Yeh, Pa-Der (TW)

(73) Assignees: Kuo-Yuan Chang, Taipei Hsien (TW); Kuo-Ku Chang, Taipei Hsien (TW)

( * ) Notice: Subject to any disclaimer, the term of this patent is extended or adjusted under 35 U.S.C. 154(b) by 486 days.

(21) Appl. No.: 10/345,485

(22) Filed: Jan. 17, 2003

(65) Prior Publication Data
US 2004/0143192 A1    Jul. 22, 2004

(51) Int. Cl.
*A61B 5/02* (2006.01)
(52) U.S. Cl. .................................... 600/508
(58) Field of Classification Search ............... 128/904; 600/513, 515, 518, 509, 501, 502, 503, 504, 600/500, 508
See application file for complete search history.

(56) References Cited

U.S. PATENT DOCUMENTS

| 4,680,708 A | * | 7/1987 | Ambos et al. | 600/509 |
| 5,238,001 A | * | 8/1993 | Gallant et al. | 600/513 |
| 5,755,671 A | * | 5/1998 | Albrecht et al. | 600/516 |

* cited by examiner

*Primary Examiner*—Mark Bockelman
(74) *Attorney, Agent, or Firm*—Rosenberg, Klein & Lee

(57) ABSTRACT

A heart state monitor method is proposed. The physiologic parameter of a life body is measured and then preformed by Fourier transform analysis. Next, the frequency domain data of the physiologic parameter are converted into a power spectral density (PSD). A heart beat noise index of the life body is then obtained according to the PSD. Finally, the heart state of the life body is diagnosed according to the heart beat noise index. The heart beat noise index may be quickly discriminated to let the life body and medical staffs grasp the current heart state of the life body at any time.

9 Claims, 10 Drawing Sheets

HEART STATE MONITOR METHOD

FIELD OF THE INVENTION

The present invention relates to a heart state monitor method and, more particularly, to a monitor method capable of quickly and easily measuring and grasping the heart state of a life body at any time.

BACKGROUND OF THE INVENTION

Cardiovascular diseases are one of the primary pathogenic factors of people all the time. In addition to age, high blood fat, high cholesterol in the blood, hypertension, diabetes and heredity, people having a too high content of fat due to smoking, lack of exercise, fatness and abnormal diet may easily catch cardiovascular diseases.

Cardiovascular diseases are basically measured by apparatuses. In the prior art, an electrocardiogram of a heart is measured by an apparatus to determine which situation a patient suffers from. Usually, the patient lies quietly on a bed for a static electrocardiogram. However, such variation like the arrhythmia or coronary disease occurs only when or after people take exercise. This kind of inspection is called an exercise electrocardiogram. Besides, because the arrhythmia or coronary disease may occur at any time in a day, an apparatus is taken along the patient all the day for grasping data momentarily. This kind of inspection is called an all-day electrocardiogram. However, either exercise electrocardiogram or the all-day electrocardiogram is very cumbersome for the patient. Moreover, because the cardiovascular diseases do not occur all the time, it is sometimes difficult to find them. Many people may have cardiovascular disease and be unaware, hence allowing cardiovascular disease to become silent killers of otherwise healthy individuals.

Beside the above drawbacks, when using a conventional measurement apparatus to measure the heart state, the patient needs to take off his/her clothes so that sticking sheets of the measurement apparatus can adhere to the vicinity of the heart for obtaining an electrocardiogram. This is very inconvenient for the patient, especially for a female patient. Moreover, the measured result of a conventional heart measurement apparatus can only be analyzed by medical staffs. Once the body of a patient has a bad status when he/she goes out for work or play, because the medical staffs cannot grasp the physiologic status of the patient immediately, it is usually too late for the patient to take medical treatment.

Accordingly, the present invention aims to propose a heart state monitor method to let a patient be able to measure and determine the health state of his heart at any time himself so as to resolve the problems in the prior art.

SUMMARY AND OBJECTS OF THE PRESENT INVENTION

The primary object of the present invention is to propose a heart state monitor method, which makes use of measurement of the heart beat of a life body at his arm, wrist, finger or ankle to accurately know the heart status of the life body after numerical processing. The life body can thus easily perform measurement and accurately obtain the health state of his heart.

Another object of the present invention is to propose a heart state monitor method, which can transmit the measured physiologic parameter of a life body to a medical center via a transmission circuit, and can record and analyze the current heart state of the life body in real time. The current heart state of the life body can thus be easily measured and accurately recorded at any place so that the life body and medical staffs can grasp the current heart state of the life body and thereby make real-time and effective treatment.

To achieve the above objects, the present invention comprises the following steps. First, a physiologic parameter of a life body is measured. The physiologic parameter is transformed by means of Fourier transform and then converted into a power spectral density (PSD). A heart beat noise index of the life body is then obtained according to the PSD. Finally, the heart state of the life body is diagnosed according to the heart beat noise index.

Another embodiment of the present invention comprises the following steps. First, a physiologic parameter of a life body is measured. The physiologic parameter is then analyzed to obtain envelope functions thereof. Next, a roughness integral (Ri) and a roughness differential (Rd) are calculated out according to the envelope functions. Finally, the heart state of the life body is diagnosed according to the roughness integral and the roughness differential.

The various objects and advantages of the present invention will be more readily understood from the following detailed description when read in conjunction with the appended drawings, in which:

DETAILED DESCRIPTION OF PREFERRED EMBODIMENT

Figure 1:
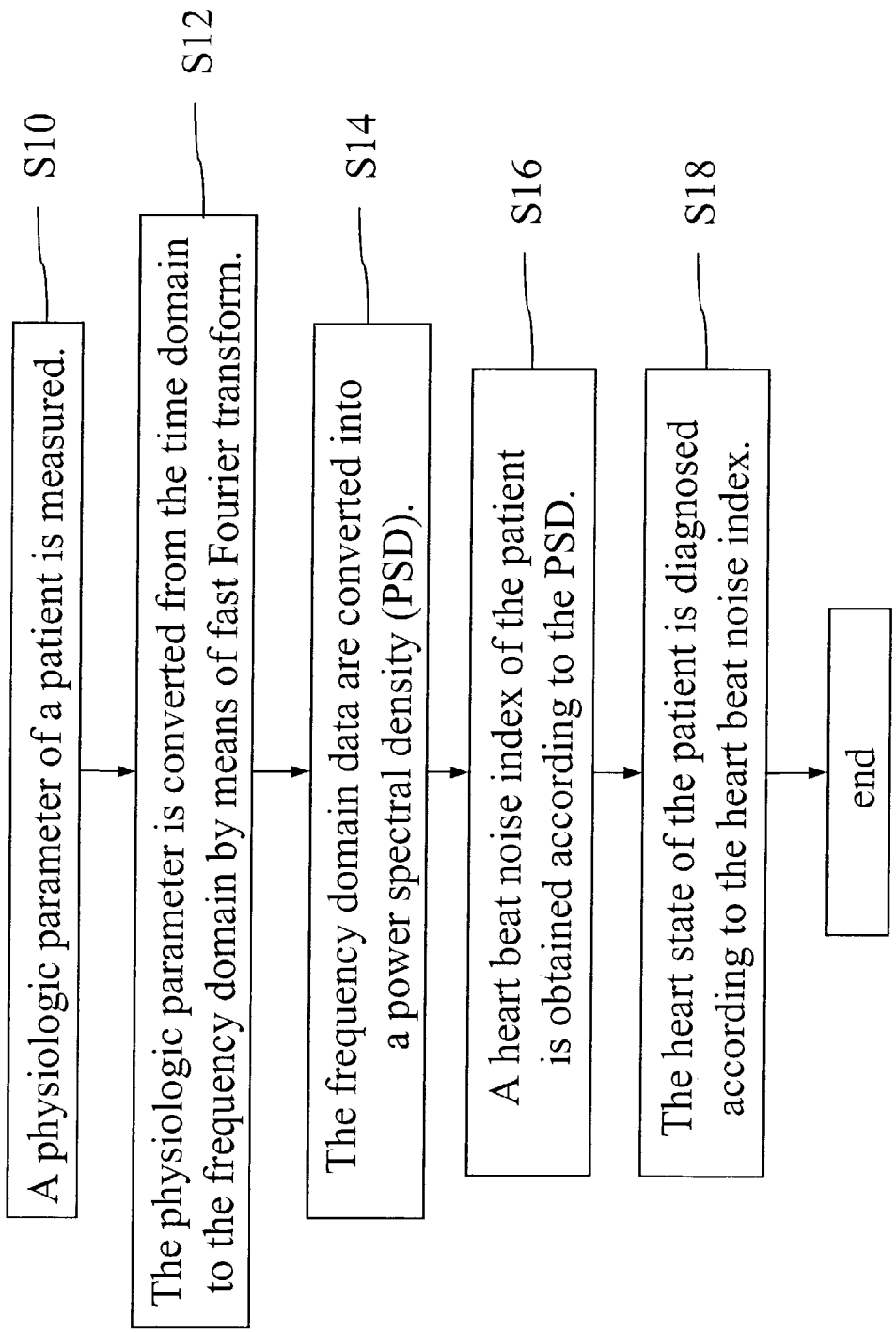
FIG. 1 shows a flowchart of the present invention.

As shown in FIG. 1, a heart state monitor method of the present invention comprises the following steps. First, the arm of a patient is measured to obtain a physiologic parameter like the heart beat signal (Step S10). The physiologic parameter is then transmitted to a medical center via a transmission circuit. The medical center transforms the received physiologic parameter from the time domain to the frequency domain by means of Fourier transform, and then integrates and stores these data into a database (Step S12).

The frequency domain data are then converted into a power spectral density (PSD) (Step S14). Next, a heart beat noise index of the patient is calculated out according to many noise waveforms between harmonics in the PSD (Step S16). Finally, the heart state of the patient is diagnosed according to the heart beat noise index (Step S18).

In addition to the arm, the wrist, finger or ankle of a patient can also be measured to obtain a physiologic parameter of the patient. Or an infrared physiology measurement device can further be utilized for measurement. Besides, the transmission circuit can be a telephone circuit, an integrated service digital network (ISDN), an asymmetrical digital subscriber loop (ADSL), a high-speed digital subscriber loop (HDSL), a transmission control protocol/Internet protocol (TCP/IP), a cable circuit, an infrared transmission circuit or a radio-frequency (RF) transmission circuit.

In addition to measuring the physiologic state of heart by a patient himself, the present invention can also transmit the patient's physiologic parameter to a medical center for analysis. Therefore, no matter the patient is at home or goes out for work or playing, he can perform measurement and then transmit the measured physiologic parameter to the location of a medical center or medical staffs if necessary to let them grasp his status at any time. Additionally, the physiologic parameter of the patient can also be transmitted to any medical equipment or device for analysis and storage of the physiologic parameter.

The present invention is cooperated with National Taiwan University, ROC for research and development, and Cathay General Hospital, ROC is then entrusted for experiments. First, a testee without any heart disease is measured with the above method to obtain heart beat signal data of this testee. The data are heart beat signals with respect to time as shown in the table below:

| | | | | | | | |
|---|---|---|---|---|---|---|---|
| 150.5829 | 317.6681 | −447.623 | 22.69058 | 20.6278 | 105.2018 | 51.5695 | 78.38564 |
| 18.56502 | 655.9641 | −447.623 | 33.00448 | 6.18834 | 113.4529 | 55.69506 | 47.44394 |
| 26.81614 | 606.4573 | −402.242 | 37.13004 | 4.12556 | 84.57398 | 59.82062 | 30.9417 |
| 66.00896 | 198.0269 | −200.09 | 43.31838 | −2.06278 | 39.19282 | 61.8834 | 41.2556 |
| 24.75336 | −257.848 | −88.6995 | 121.704 | 2.06278 | 24.75336 | 59.82062 | 49.50672 |
| 6.18834 | −447.623 | −39.1928 | 99.01344 | 16.50224 | 30.9417 | 72.1973 | 47.44394 |
| 18.56502 | −307.354 | −2.06278 | 55.69506 | 22.69058 | 33.00448 | 129.9551 | 45.38116 |
| 22.69058 | −80.4484 | 6.18834 | 24.75336 | 72.1973 | 30.9417 | 88.69954 | 39.19282 |
| 20.6278 | −18.565 | 18.56502 | 22.69058 | 138.2063 | 30.9417 | 45.38116 | 43.31838 |
| 18.56502 | −41.2556 | 30.9417 | 16.50224 | 99.01344 | 30.9417 | 22.69058 | 66.00896 |
| 24.75336 | −16.5022 | 35.06726 | 12.37668 | 59.82062 | 28.87892 | 24.75336 | 105.2018 |
| 24.75336 | 12.37668 | 74.26008 | 14.43946 | 18.56502 | 43.31838 | 33.00448 | 80.44842 |
| 20.6278 | 12.37668 | 94.88788 | 37.13004 | 18.56502 | 115.5157 | 33.00448 | 59.82062 |
| 57.75784 | 14.43946 | 45.38116 | 49.50672 | 26.81614 | 96.95066 | 30.9417 | 41.2556 |
| 76.32286 | 20.6278 | 6.18834 | 57.75784 | 24.75336 | 63.94618 | 30.9417 | 51.5695 |
| 14.43946 | 26.81614 | −6.18834 | 125.8296 | 22.69058 | 35.06726 | 28.87892 | 53.63228 |
| −4.12556 | 28.87892 | 12.37668 | 152.6457 | 24.75336 | 35.06726 | 30.9417 | 51.5695 |
| 12.37668 | 30.9417 | 28.87892 | 105.2018 | 26.81614 | 41.2556 | 99.01344 | 43.31838 |
| 26.81614 | 66.00896 | 24.75336 | 68.07174 | 43.31838 | 35.06726 | 101.0762 | 43.31838 |
| 22.69058 | 82.5112 | 24.75336 | 33.00448 | 134.0807 | 35.06726 | 72.1973 | 43.31838 |
| 22.69058 | 35.06726 | 30.9417 | 6.18834 | 111.3901 | 30.9417 | 37.13004 | 66.00896 |
| 24.75336 | −14.4395 | 28.87892 | −6.18834 | 70.13452 | 33.00448 | 26.81614 | 86.63676 |
| 28.87892 | 3.81E−07 | 59.82062 | −4.12556 | 26.81614 | 43.31838 | 37.13004 | 68.07174 |
| 24.75336 | 24.75336 | 125.8296 | 4.12556 | 24.75336 | 55.69506 | 43.31838 | 45.38116 |
| 35.06726 | 30.9417 | 72.1973 | 18.56502 | 33.00448 | 111.3901 | 39.19282 | 39.19282 |
| 84.57398 | 33.00448 | 37.13004 | 28.87892 | 37.13004 | 84.57398 | 33.00448 | 47.44394 |
| 68.07174 | 226.9058 | 4.12556 | 96.95066 | 26.81614 | 51.5695 | 33.00448 | 53.63228 |
| 16.50224 | 996.3228 | 2.06278 | 129.9551 | 30.9417 | 24.75336 | 37.13004 | 49.50672 |
| −8.25112 | 1014.888 | 6.18834 | 94.88788 | 24.75336 | 37.13004 | 68.07174 | 49.50672 |
| 39.19282 | 253.7219 | 16.50224 | 53.63228 | 33.00448 | 51.5695 | 111.3901 | 51.5695 |
| | 51.5695 | 45.38116 | 30.9417 | 84.57398 | 47.44394 | 63.9462 | 66.00896 |
| | 82.5112 | 49.50672 | 49.50672 | 94.88788 | 49.50672 | 59.8206 | 63.94618 |
| | 84.57398 | 49.50672 | 70.13452 | 78.38564 | 49.50672 | 55.6951 | 68.07174 |
| | 63.94618 | 63.94618 | 59.82062 | 63.94618 | 72.1973 | 66.009 | 68.07174 |
| | 43.31838 | 80.44842 | 57.75784 | 63.94618 | 72.1973 | 66.009 | 72.1973 |
| | 49.50672 | 66.00896 | 61.8834 | 76.32286 | 72.1973 | 84.574 | 84.57398 |
| | 57.75784 | 53.63228 | 51.5695 | 72.1973 | 61.8834 | 84.574 | 103.139 |
| | 66.00896 | 47.44394 | 63.94618 | 57.75784 | 59.82062 | 88.6995 | 109.3273 |
| | 63.94618 | 53.63228 | 80.44842 | 51.5695 | 57.75784 | 88.6995 | 94.88788 |
| | 63.94618 | 59.82062 | 66.00896 | 45.38116 | 55.69506 | 99.0134 | 76.32286 |
| | 66.00896 | 61.8834 | 51.5695 | 45.38116 | 55.69506 | 80.4484 | 61.8834 |
| | 70.13452 | 59.82062 | 51.5695 | 51.5695 | 59.82062 | 66.009 | 53.63228 |
| | 105.2018 | 74.26008 | 51.5695 | 70.13452 | 61.8834 | 53.6323 | 53.63228 |
| | 96.95066 | 86.63676 | 51.5695 | 63.94618 | 63.94618 | 51.5695 | 53.63228 |
| | 90.76232 | 92.8251 | 53.63228 | 45.38116 | 76.32286 | 57.7578 | 57.75784 |
| | 72.1973 | 82.5112 | 49.50672 | 47.44394 | 68.07174 | 70.1345 | 61.8834 |
| | 78.38564 | 57.75784 | 49.50672 | 53.63228 | 61.8834 | 70.1345 | 55.69506 |
| | 70.13452 | 45.38116 | 63.94618 | 53.63228 | 53.63228 | 57.7578 | 74.26008 |
| | 53.63228 | 22.69058 | 66.00896 | 55.69506 | 61.8834 | 55.6951 | 68.07174 |
| | 39.19282 | 45.38116 | 80.44842 | 59.82062 | 63.94618 | 59.8206 | 55.69506 |
| | 41.2556 | 49.50672 | 72.1973 | 68.07174 | 61.8834 | 63.94618 | 66.00896 |
| | 43.31838 | 49.50672 | 59.82062 | 84.57398 | 61.8834 | 57.75784 | 61.8834 |
| | 53.63228 | 59.82062 | 49.50672 | 113.4529 | 59.82062 | 53.63228 | 72.1973 |
| | 76.32286 | 68.07174 | 53.63228 | 136.1435 | 63.94618 | 55.69506 | 63.94618 |

-continued

| | | | | | | |
|---|---|---|---|---|---|---|
| 61.8834 | 53.63228 | 61.8834 | 113.4529 | 74.26008 | 51.5695 | 68.07174 |
| 51.5695 | 59.82062 | 66.00896 | 88.69954 | 84.57398 | 66.00896 | 70.13452 |
| 43.31838 | 59.82062 | 63.94618 | 55.69506 | 70.13452 | 76.32286 | 68.07174 |
| 51.5695 | 76.32286 | 68.07174 | 47.44394 | 66.00896 | 72.1973 | 74.26008 |
| 51.5695 | 63.94618 | 66.00896 | 49.50672 | 59.82062 | 68.07174 | 99.01344 |
| 49.50672 | 49.50672 | 70.13452 | 45.38116 | 63.94618 | 59.82062 | 76.32286 |

Figure 2A:
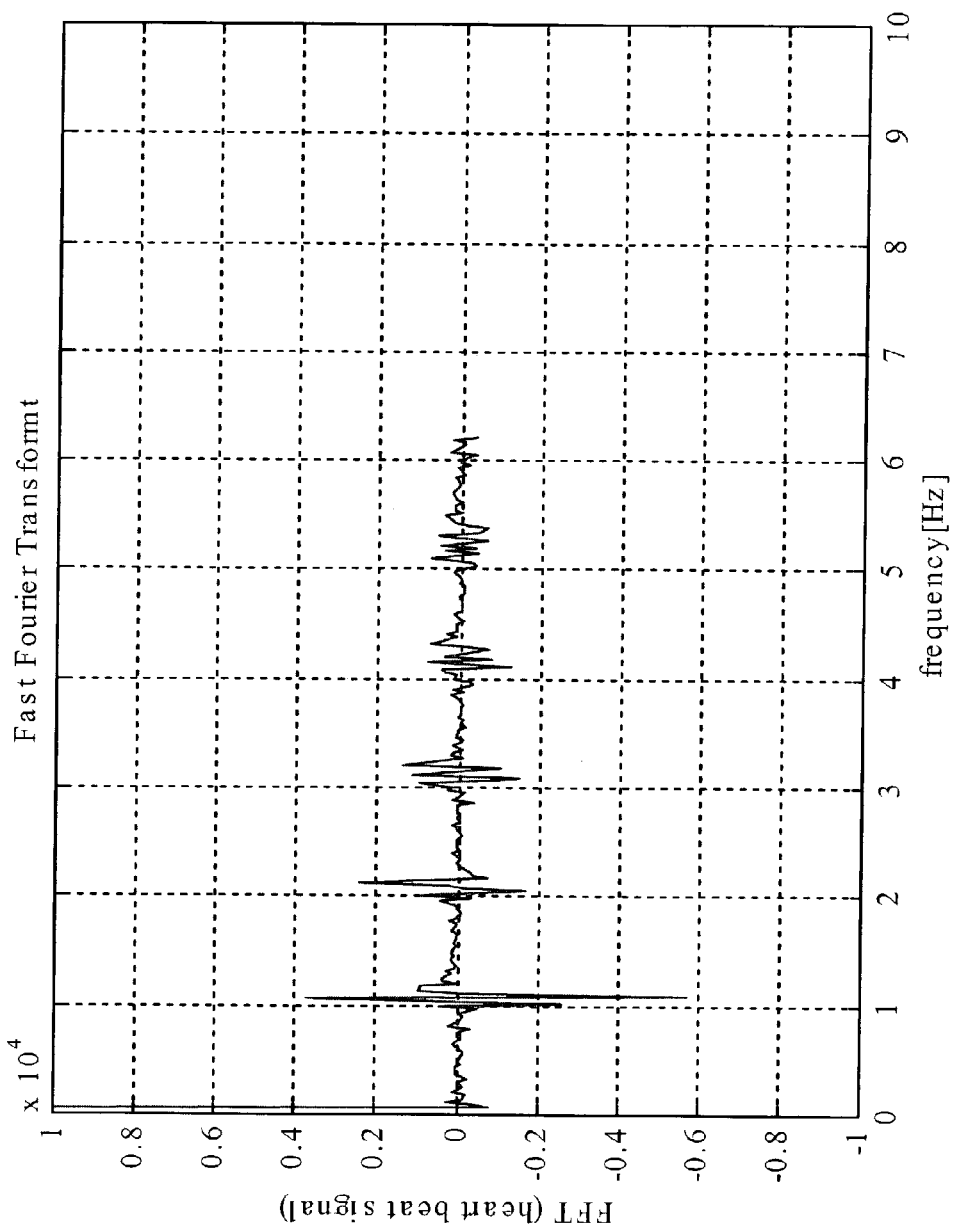
FIG. 2A shows the Fourier transform of the heart beat signal of a testee without any heart disease.
Figure 2B:
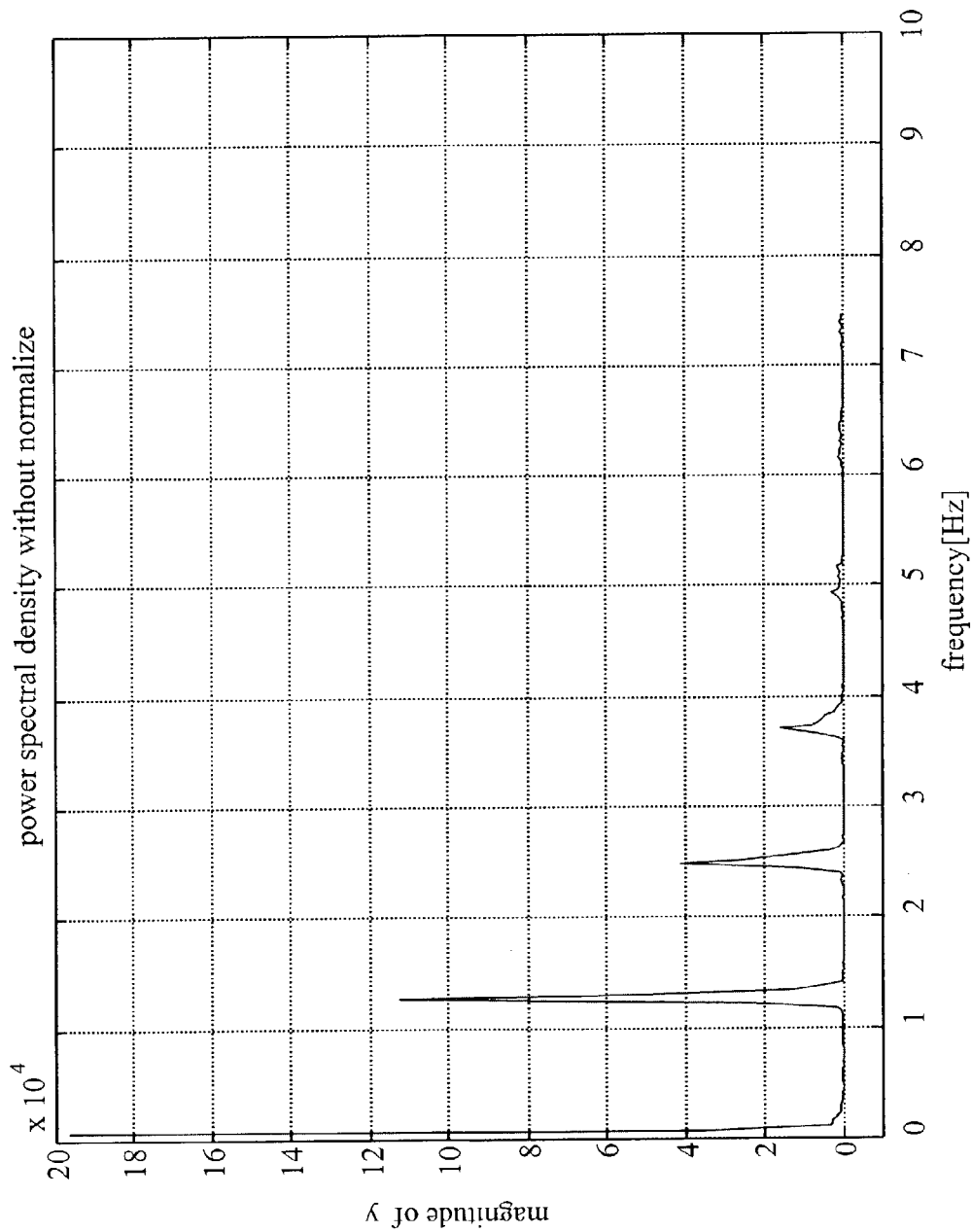
FIG. 2B is a power spectral density graph of FIG. 2A.
Figure 3:
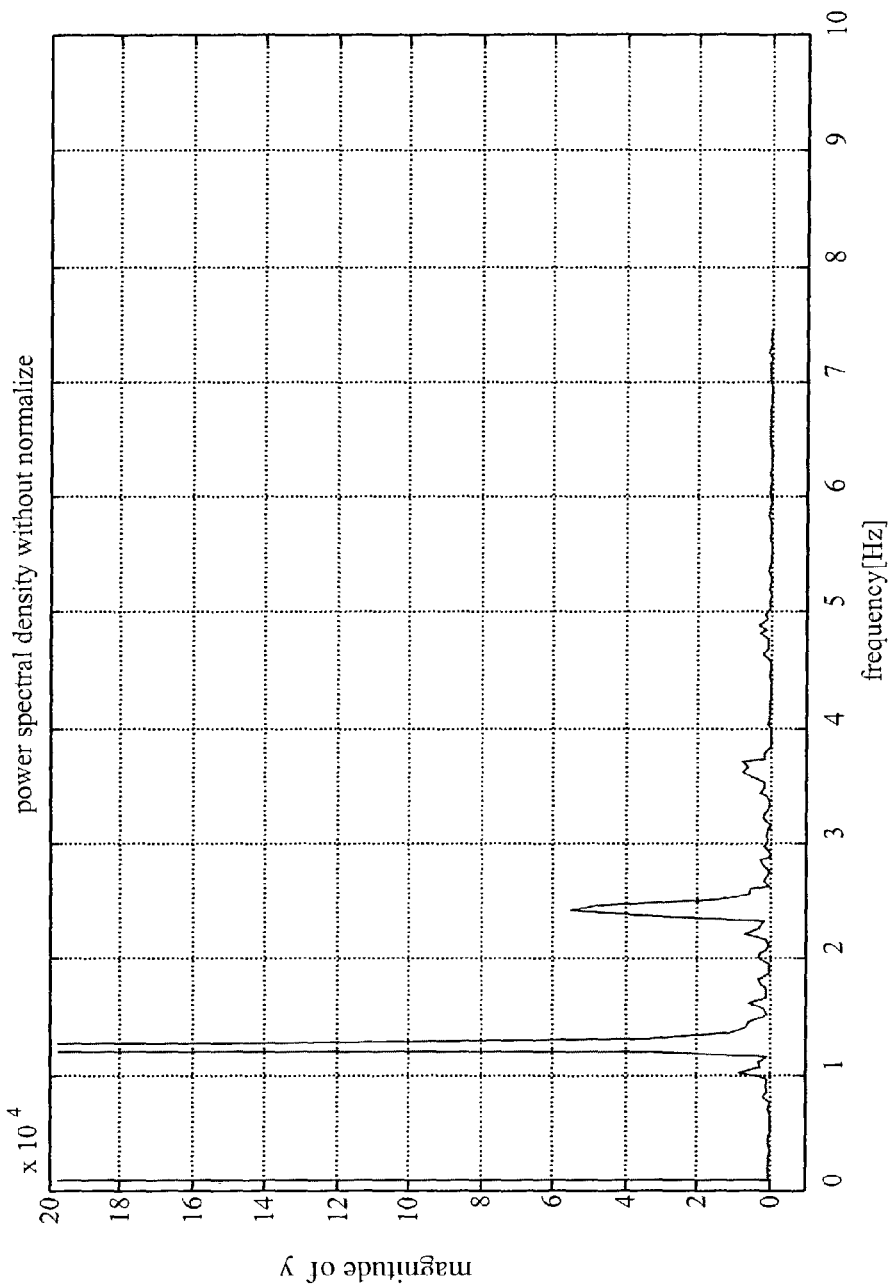
FIG. 3 is a power spectral density graph of a patient with Atrial Fib. (AF)
Figure 4:
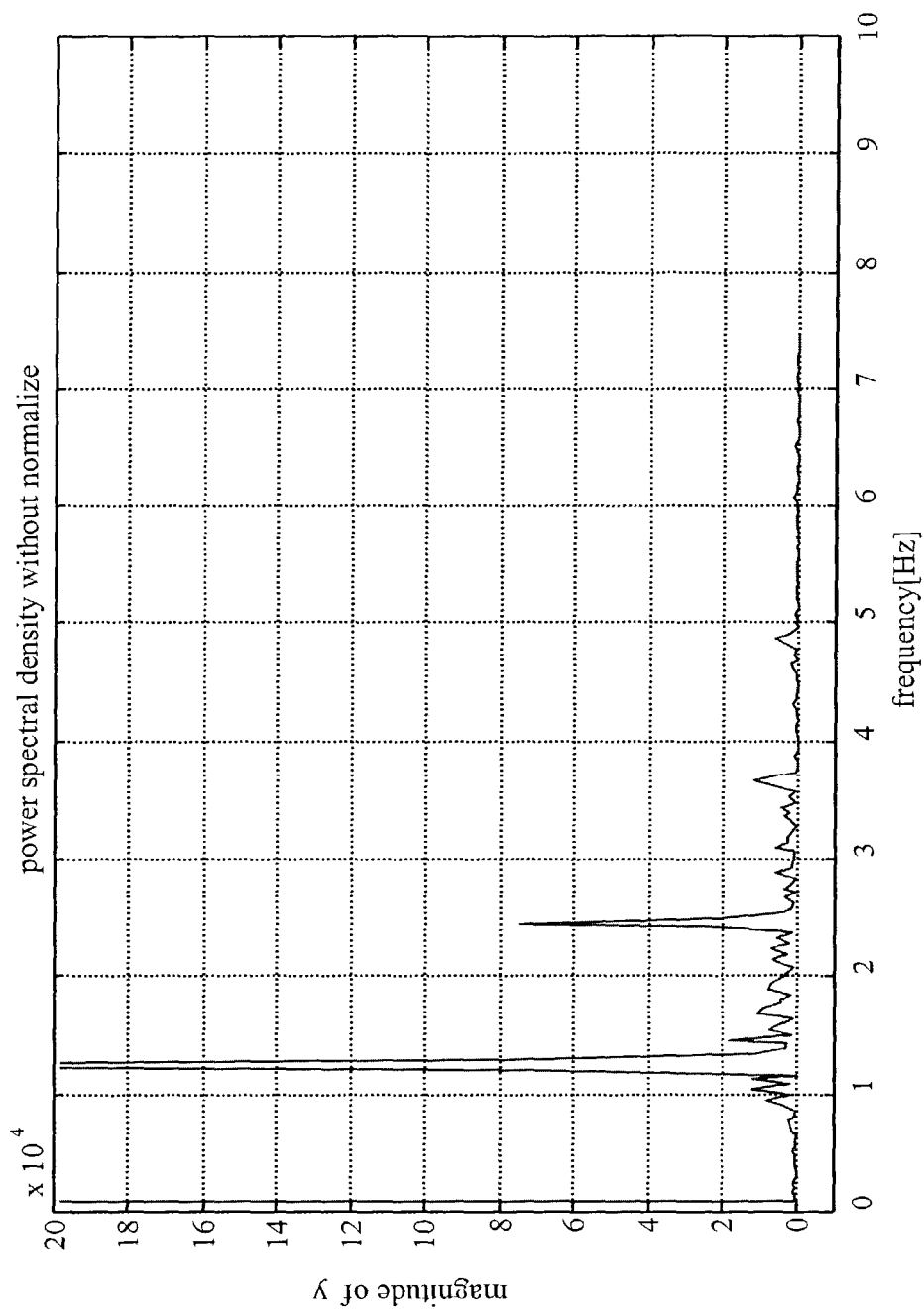
FIG. 4 is a power spectral density graph of a patient with entricular (PVC)
Figure 5:
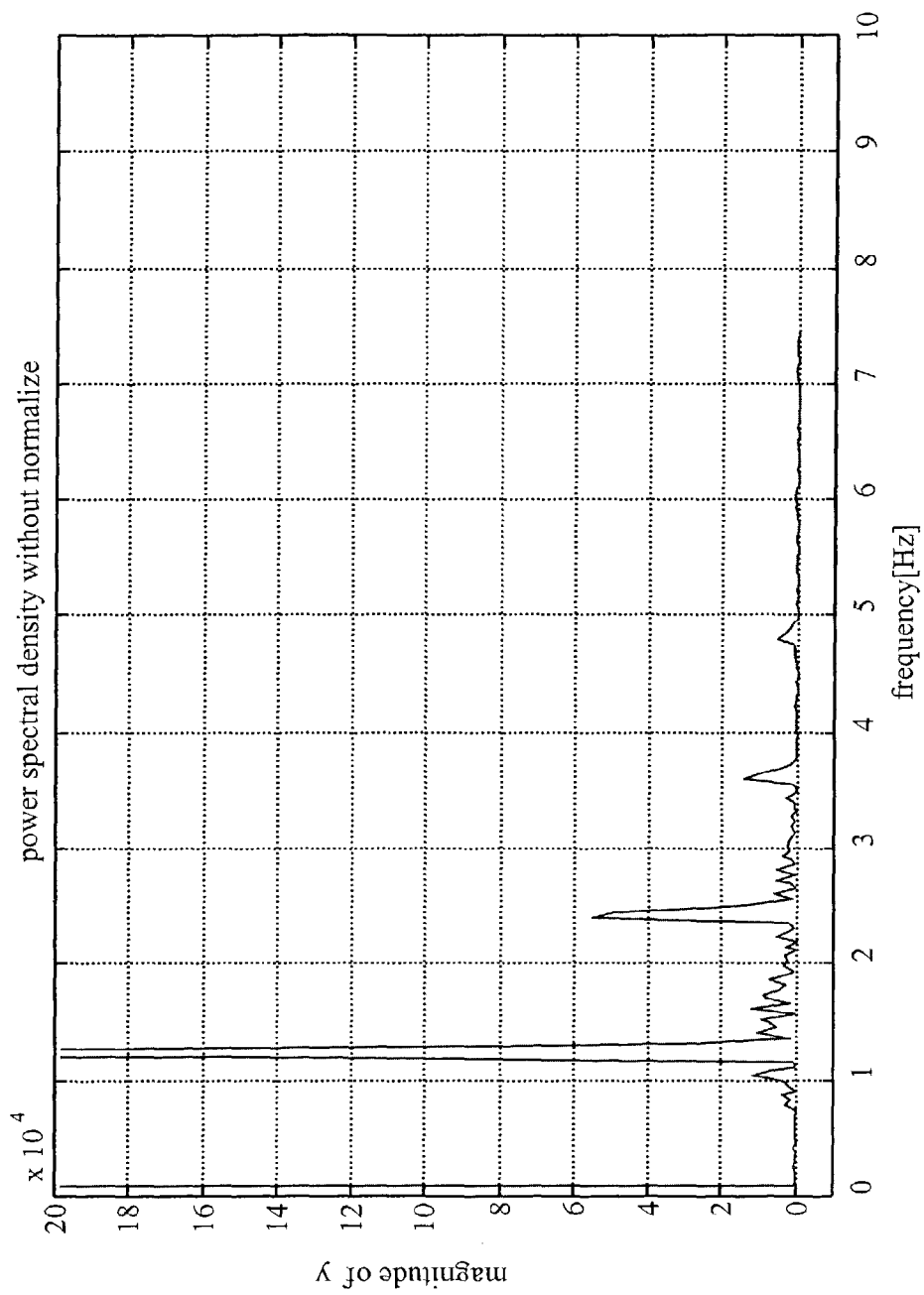
FIG. 5 is a power spectral density graph of a patient with Atrial (PAC)

Next, the heart beat signal data in the table are converted from the time domain to the frequency domain by means of Fourier transform to obtain the frequency domain data shown in FIG. 2A. Finally, the frequency domain data shown in FIG. 2A are converted into a power spectral density (PSD) graph shown in FIG. 2B. As can be known from this figure, a flat waveform exists between each harmonic when the heart has no disease. However, there exist many noise waveforms between harmonics in the PSD graph if the heart has a disease. As shown in FIG. 3, the number of noise waveforms between harmonics in the PSD graph of a patient having Atrial Fib. (AF) is larger than that of a normal person. As shown in FIG. 4, the number of noise waveforms between harmonics in the PSD graph of a patient having entricular (PVC) is larger than that of a patient having Atrial Fib. (AF). As shown in FIG. 5, the number of noise waveforms between harmonics in the PSD graph of a patient having Atrial (PAC) is larger than that of a patient having entricular (PVC).

From FIGS. 2B, 3, 4 and 5, we can know that the number of noise waveforms between each harmonic increases with the order of severity of the heart state. Therefore, noise waveforms between each harmonic can be utilized to calculate out a heart beat noise index of each patient. The health status of a patient can thus be determined according to the heart beat noise index. Accuracy and practicability of the present invention have been verified by cooperation with National Taiwan University, ROC for two years and experiments of Cathay General Hospital, ROC.

In addition to converting heart beat signals into a PSD for calculation and analysis of the heart beat noise index of a patient, the heart beat signal curve can also undergo an analysis of envelope function. This embodiment of the present invention comprises the following steps. First, a physiologic parameter like the heart beat signal of a patient is measured. The physiologic parameter is then analyzed to obtain envelope functions thereof. Next, a roughness integral (Ri) and a roughness differential (Rd) are calculated out according to the envelope functions. Finally, the heart state of the patient is diagnosed according to the roughness integral and the roughness differential.

Figure 6A:
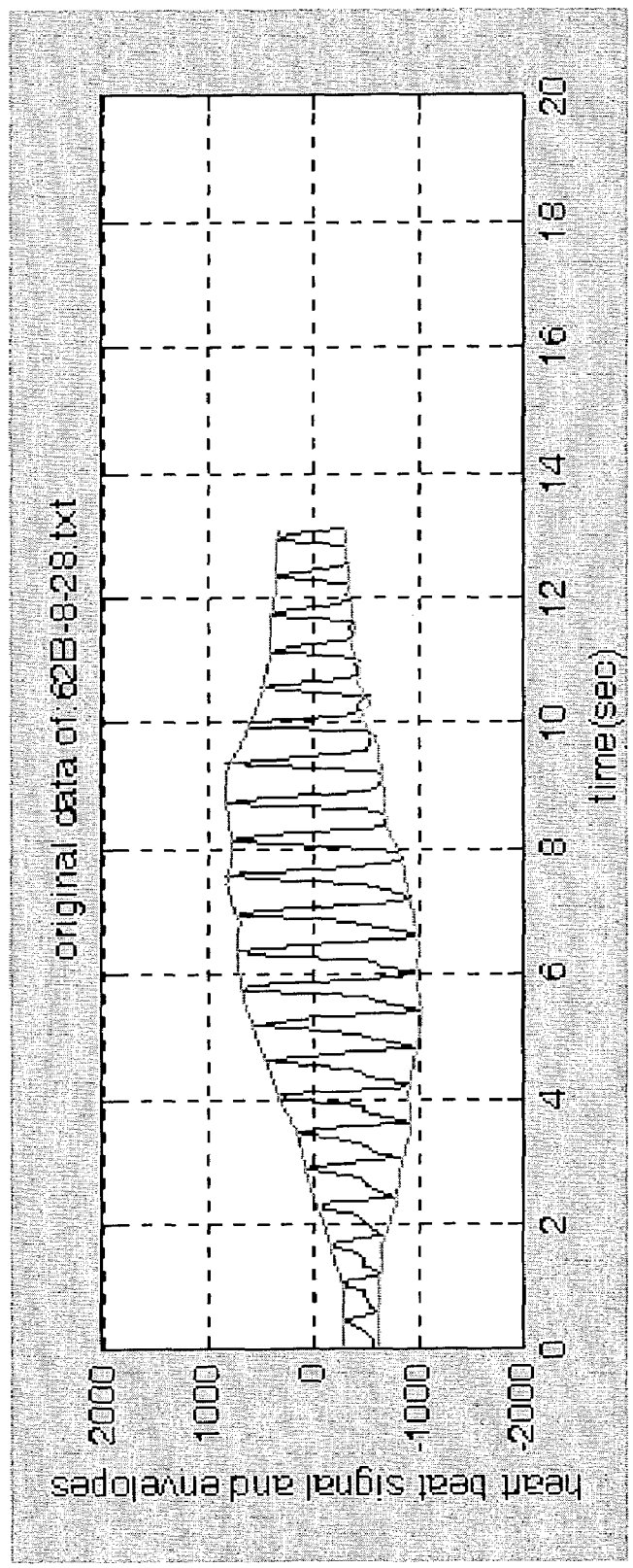
FIG. 6A shows envelopes of the heart beat signal of a testee without any heart disease.
Figure 6B:
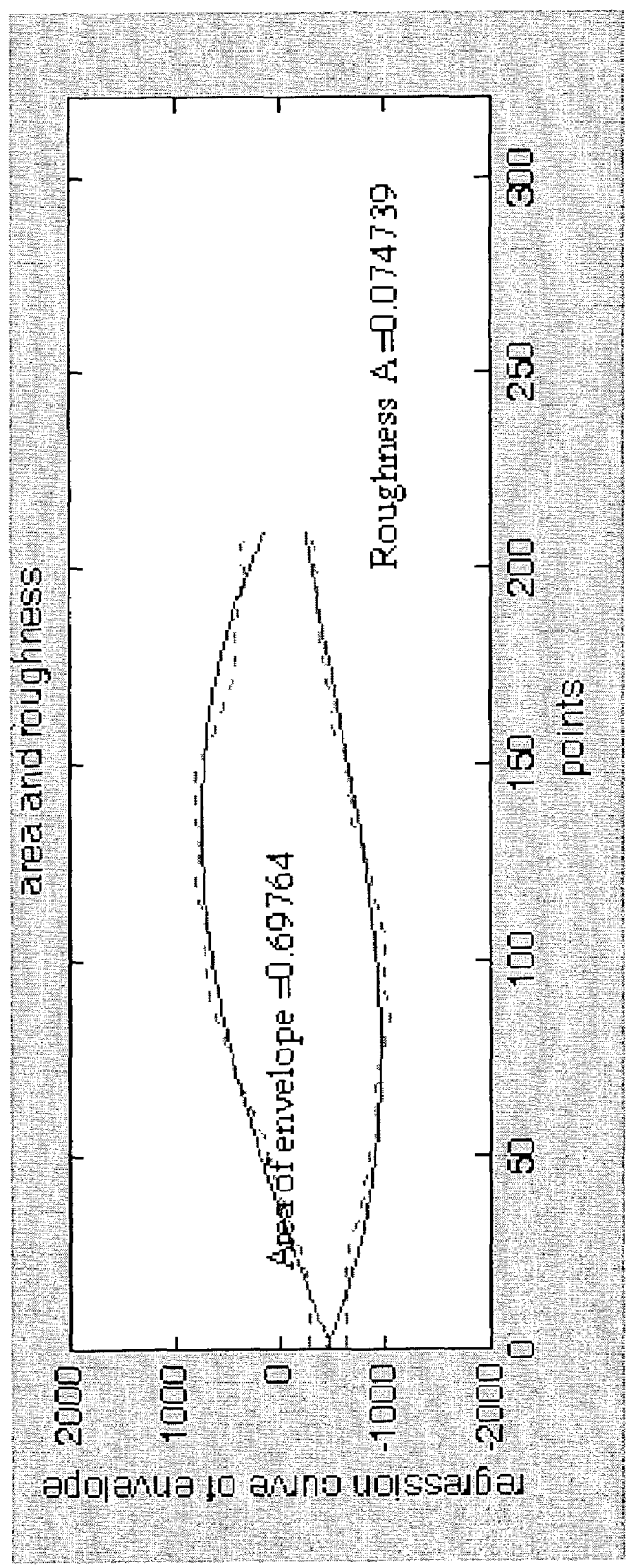
FIG. 6B shows the area enclosed by the envelopes in FIG. 6A after time-domain integral.
Figure 7A:
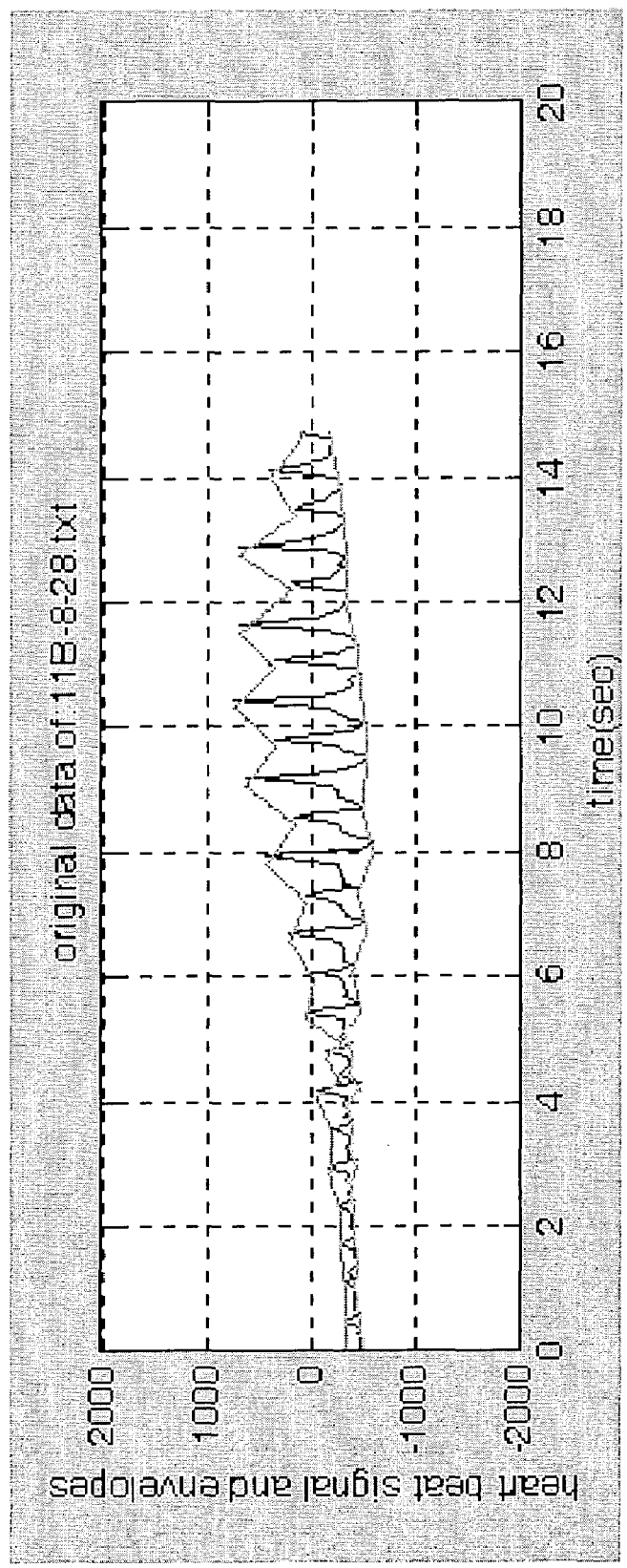
FIG. 7A shows envelopes of the heart beat signal of a patient with cardiomyopathy.
Figure 7B:
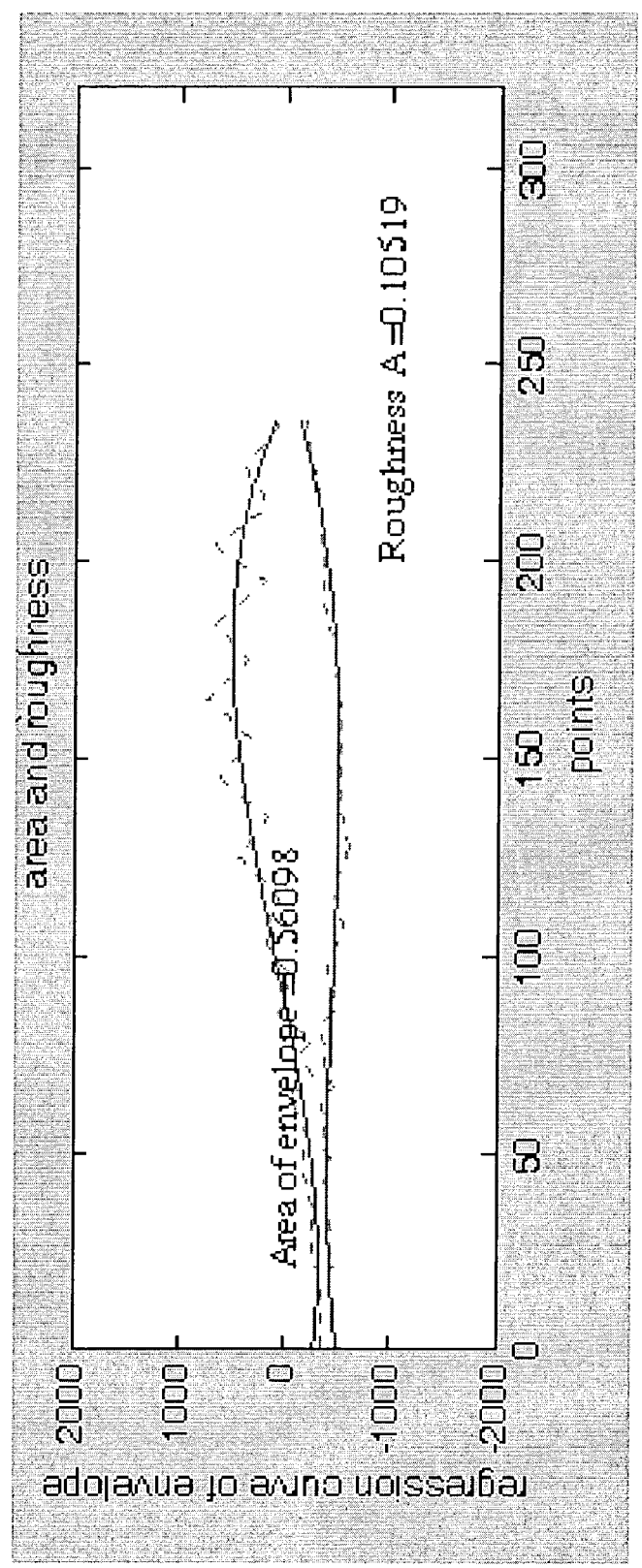
FIG. 7B shows the area enclosed by the envelopes in FIG. 7A after time-domain integral.

FIG. 6A shows envelopes of heart beat signal data of a testee without any heart disease. The area enclosed by the envelope of FIG. 6A is then integrated to obtain the area enclosed by the envelope and calculate out a roughness integral (Ri), as shown in FIG. 6B. The Ri of the testee without any heart disease is 0.074739. Next, FIG. 7A shows envelopes of heart beat signal data of a patient with cardiomyopathy. The area enclosed by the envelope of FIG. 7A is then integrated to obtain the area enclosed by the envelope and calculate out a roughness integral (Ri), as shown in FIG. 7B. The Ri of the patient with cardiomyopathy is 0.10519. Through comparison, it is evident the Ri of the patient with heart disease is larger than that of the testee without any heart disease. Cathay General Hospital, ROC measured many testees without any heart disease and many patients with valve disease or cardiomyopathy to obtain the following table:

| Type | File name | Integral of normalized area | Ri | Type | File name | Integral of normalized area | Ri |
|---|---|---|---|---|---|---|---|
| Healthy heart | 9-8-28 | 0.72696 | 0.04032 | Valve disease | 8-8-28 | 0.72859 | 0.05797 |
| | 21-8-28 | 0.70771 | 0.04595 | | 54-8-28 | 0.71496 | 0.19529 |
| | 25-8-28 | 0.72304 | 0.06440 | | 78-8-28 | 0.66857 | 0.13034 |
| | 26-8-28 | 0.73554 | 0.06750 | | 4-8-30 | 0.77257 | 0.07005 |
| | 33-8-28 | 0.70940 | 0.12065 | | 15-8-30 | 0.69496 | 0.15187 |
| | 52-8-28 | 0.71541 | 0.07768 | | 20-8-30 | 0.65289 | 0.27694 |
| | 67-8-28 | 0.75890 | 0.06634 | | 31-8-30 | 0.64088 | 0.23327 |
| | 72-8-28 | 0.75650 | 0.06634 | | 64-8-30 | 0.65289 | 0.27694 |
| | 95-8-28 | 0.77309 | 0.03792 | | 44-9-4 | 0.73418 | 0.04754 |
| | 99-8-28 | 0.72481 | 0.078335 | | 64-9-4 | 0.65289 | 0.27694 |
| | 5-8-30 | 0.74556 | 0.06534 | | 68-9-4 | 0.59276 | 0.15297 |
| | 12-8-30 | 0.70205 | 0.15187 | | 70-9-4 | 0.81891 | 0.12632 |
| | 18-8-30 | 0.65404 | 0.13052 | Mean | | 0.69375 | 0.16637 |
| | 23-8-30 | 0.67276 | 0.13320 | Standard deviation | | 0.06311 | 0.08551 |
| | 32-8-30 | 0.73545 | 0.08168 | Cardiomyopathy | 5-8-28 | 0.66557 | 0.14648 |
| | 48-8-30 | 0.78127 | 0.04743 | | 11-8-28 | 0.56098 | 0.10519 |
| | 50-8-28 | 0.69595 | 0.08872 | | 13-8-28 | 0.71496 | 0.19529 |
| | 59-8-30 | 0.71071 | 0.09931 | | 3-8-30 | 0.71364 | 0.07890 |
| | 7-9-4 | 0.73095 | 0.06975 | | 21-8-30 | 0.66731 | 0.23981 |
| | 18-9-4 | 0.72239 | 0.07027 | | 37-8-30 | 0.63333 | 0.23693 |
| | 22-9-4 | 0.70103 | 0.04272 | | 57-8-30 | 0.70211 | 0.28642 |
| | 53-9-4 | 0.74003 | 0.12303 | | 80-8-30 | 0.64971 | 0.10831 |
| | 56-9-4 | 0.72689 | 0.09979 | | 15-9-4 | 0.65891 | 0.18309 |
| | 60-9-4 | 0.71768 | 0.05073 | | 19-9-4 | 0.63151 | 0.22443 |
| | 61-9-4 | 0.76758 | 0.07225 | | 21-9-4 | 0.71839 | 0.19035 |

-continued

| Type | File name | Integral of normalized area | Ri | Type | File name | Integral of normalized area | Ri |
|---|---|---|---|---|---|---|---|
| | Mean | 0.72543 | 0.07968 | | Mean | 0.66513 | 0.18138 |
| | Standard deviation | 0.03071 | 0.032996 | | Standard deviation | 0.04723 | 0.06521 |

As can be known from the table, the mean of the roughness integral Ri of healthy hearts is 0.07968, the mean of the roughness integral Ri of hearts with valve disease is 0.16637, and the mean of the roughness integral Ri of hearts with is cardiomyopathy is 0.18138. Similarly, it is evident the Ri of the patients with heart disease is larger than that of the testees without any heart disease. Therefore, heart diseases like valve disease and cardiomyopathy of a patient can be determined based on the Ri value of his heart.

Moreover, the envelope function of the heart beat signals of a patient can be differentiated to obtain the roughness differential. Similarly, heart diseases like valve disease and cardiomyopathy of a patient can be determined based on the magnitude of the Rd value of his heart.

To sum up, the present invention proposes a heart state monitor method, which makes use of heart beat measurement of a life body at the arm, wrist, finger or ankle to obtain a heart beat noise index after numerical processing so as to accurately know the heart status of the life body without the inconvenience of taking off clothes. The life body can thus easily perform measurement and accurately obtain the health status of heart. Moreover, the present invention can transmit the measured heart physiologic parameter of a life body to a medical center via a transmission circuit, and can record and analyze the current heart state of the life body in real time. The life body can thus easily measure and accurately record the current heart state at any place to let the life body and medical staffs grasp the current heart state of the life body and make real-time and effective treatment.

Although the present invention has been described with reference to the preferred embodiments thereof, it will be understood that the invention is not limited to the details thereof. Various substitutions and modifications have been suggested in the foregoing description, and other will occur to those of ordinary skill in the art. Therefore, all such substitutions and modifications are intended to be embraced within the scope of the invention as defined in the appended claims.

We claim:

1. A heart state monitor method comprising the steps of: (a) measuring a physiologic parameter of a life body by using an infrared physiology measurement device; (b) converting said physiologic parameter from the time domain to the frequency domain by means of Fourier transform and then converting the frequency domain data into a power spectral density; (c) obtaining a heart beat noise index of said life body according to said power spectral density; and (d) diagnosing the heart state of said life body according to said heart beat noise index.

2. The heart state monitor method as claimed in claim 1, wherein said physiologic parameter is a heart beat signal.

3. The heart state monitor method as claimed in claim 1, wherein said physiologic parameter can be obtained by measuring an arm, wrist, finger or ankle of said life body.

4. The heart state monitor method as claimed in claim 1, wherein said physiologic parameter of said life body before analysis and said frequency domain data and said power spectral density after analysis can further be stored into a database.

5. The heart state monitor method as claimed in claim 1 further comprising a step of transmitting said physiologic parameter to a medical center via a transmission circuit for performing said Step (b) after said step (a).

6. The heart state monitor method as claimed in claim 5, wherein said transmission circuit is a telephone circuit, an ISDN, an ADSL, a HDSL, a TCP/IP, a cable circuit, an infrared transmission circuit or an radio-frequency transmission circuit.

7. The heart state monitor method as claimed in claim 1, wherein many noise waveforms between each harmonic in said power spectral density can further be used to calculate out said heart beat noise index of said life body.

8. A heart state monitor method comprising the steps of: (a) measuring a physiologic parameter of a life body; (b) analyzing said physiologic parameter to obtain envelope functions thereof; (c) calculating a roughness integral and a roughness differential according to said envelope functions; and (d) diagnosing the heart state of said life body according to said roughness integral and said roughness differential.

9. The heart state monitor method as claimed in claim 8, wherein said physiologic parameter can be obtained by measuring an arm, wrist, finger or ankle of said life body.

* * * * *